US012611154B2

(12) United States Patent
Tajima

(10) Patent No.: US 12,611,154 B2
(45) Date of Patent: Apr. 28, 2026

(54) RADIOGRAPHY SYSTEM, OPERATION METHOD THEREOF, AND OPERATION PROGRAM

(71) Applicant: FUJIFILM CORPORATION, Tokyo (JP)

(72) Inventor: Takashi Tajima, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 18/824,923

(22) Filed: Sep. 5, 2024

(65) Prior Publication Data

US 2025/0107766 A1 Apr. 3, 2025

(30) Foreign Application Priority Data

Sep. 28, 2023 (JP) ................................ 2023-168766

(51) Int. Cl.
A61B 6/00 (2024.01)

(52) U.S. Cl.
CPC ................ A61B 6/487 (2013.01); A61B 6/54 (2013.01); A61B 6/566 (2013.01)

(58) Field of Classification Search
CPC .......... A61B 6/487; A61B 6/54; A61B 6/566; A61B 6/4233; A61B 6/4283; A61B 6/4291; A61B 6/4405; A61B 6/542; A61B 6/545; A61B 6/548; A61B 6/56
See application file for complete search history.

(56) References Cited

U.S. PATENT DOCUMENTS

| | | | |
|---|---|---|---|
| 2010/0172468 A1* | 7/2010 | Gregerson | A61B 6/0407 |
| | | | 378/208 |
| 2011/0170669 A1* | 7/2011 | Nakatsugawa | A61B 6/56 |
| | | | 378/116 |
| 2015/0251018 A1* | 9/2015 | Tajima | G06T 5/70 |
| | | | 378/28 |
| 2020/0205767 A1 | 7/2020 | Niwa et al. | |
| 2022/0240883 A1* | 8/2022 | Kingma | A61B 6/542 |
| 2023/0068259 A1* | 3/2023 | Cui | H04N 17/002 |
| 2025/0040899 A1* | 2/2025 | Ono | A61B 6/487 |

FOREIGN PATENT DOCUMENTS

| | | |
|---|---|---|
| JP | 2011-139851 A | 7/2011 |
| JP | 2020-103872 A | 7/2020 |
| WO | 2014/142131 A1 | 9/2014 |

* cited by examiner

*Primary Examiner* — Peter Luong
(74) *Attorney, Agent, or Firm* — SOLARIS Intellectual Property Group, PLLC

(57) ABSTRACT

A radiography system executes at least one of the following: prohibiting fluoroscopy and permitting still image capturing and continuous still image capturing in accordance with switching of a communication mode from the wired communication to the wireless communication; limiting a frame rate during the continuous still image capturing to a predetermined value or less; and disabling an auto exposure control function, which transmits an irradiation stop signal for stopping irradiation with radiation via a radiation irradiation device at a point in time at which a cumulative irradiation dose with which a radiography apparatus is irradiated reaches an appropriate amount.

7 Claims, 9 Drawing Sheets

| | WIRELESS COMMUNICATION | WIRED COMMUNICATION |
|---|---|---|
| STILL IMAGE CAPTURING | PERMIT | PERMIT |
| FLUOROSCOPY | PROHIBIT | PERMIT |
| CONTINUOUS STILL IMAGE CAPTURING | PERMIT (LIMIT FRAME RATE) | PERMIT |
| AEC FUNCTION | DISABLE | ALLOW SELECTION OF ENABLING/DISABLING |
| SCATTERED RADIATION REDUCTION FUNCTION | ENABLE | ALLOW SELECTION OF ENABLING/DISABLING |

|  | WIRELESS COMMUNICATION | WIRED COMMUNICATION |
|---|---|---|
| STILL IMAGE CAPTURING | PERMIT | PERMIT |
| FLUOROSCOPY | PROHIBIT | PERMIT |
| CONTINUOUS STILL IMAGE CAPTURING | PERMIT (LIMIT FRAME RATE) | PERMIT |
| AEC FUNCTION | DISABLE | ALLOW SELECTION OF ENABLING/DISABLING |
| SCATTERED RADIATION REDUCTION FUNCTION | ENABLE | ALLOW SELECTION OF ENABLING/DISABLING |

FIG. 12

|  | WIRELESS COMMUNICATION | WIRED COMMUNICATION |
|---|---|---|
| STILL IMAGE CAPTURING | PERMIT | PERMIT |
| FLUOROSCOPY | PROHIBIT | PERMIT |
| CONTINUOUS STILL IMAGE CAPTURING | PERMIT (LIMIT FRAME RATE) | PERMIT |
| AEC FUNCTION | DISABLE | ALLOW SELECTION OF ENABLING/DISABLING |
| SCATTERED RADIATION REDUCTION FUNCTION | ALLOW SELECTION OF ENABLING/DISABLING | ALLOW SELECTION OF ENABLING/DISABLING |

RADIOGRAPHY SYSTEM, OPERATION METHOD THEREOF, AND OPERATION PROGRAM

CROSS-REFERENCE TO RELATED APPLICATIONS

The present application claims priority under 35 U.S.C. § 119 to Japanese Patent Application No. 2023-168766, filed on Sep. 28, 2023. The above application is hereby expressly incorporated by reference, in its entirety, into the present application.

BACKGROUND

1. Technical Field

The technology of the present disclosure relates to a radiography system, an operation method thereof, and an operation program.

2. Description of the Related Art

The radiography system includes a radiography apparatus, a radiation generation device, and a control device. As the radiography apparatus, there is a portable radiography apparatus that can be attached to and detached from an imaging table. In general, the portable radiography apparatus is referred to as an electronic cassette, and the control device is referred to as a console. The console and the electronic cassette are configured to communicate with each other in a wired or wireless manner.

In addition, a radiography system that enables fluoroscopy to continuously capture a radiation image in addition to still image capturing is known (see, for example, JP2011-139851A and WO2014/142131A). In addition, the radiography system may have an auto exposure control (AEC) function of monitoring a cumulative irradiation dose of radiation from the radiation generation device to the electronic cassette and stopping the radiation irradiation at a point in time at which the cumulative irradiation dose reaches an appropriate amount (for example, see JP2020-103872A).

SUMMARY

As described above, since the electronic cassette can communicate with the console in a wireless manner, the electronic cassette can be detached from the imaging table and can perform radiography. The radiography is performed after selecting an imaging function to be used for the radiography based on an imaging technique, an imaging purpose, and the like, but there is an imaging function that is not preferable to be used in wireless communication. However, in a case where a user selects the imaging function by manual operation, the user needs to refer to an operation manual or the like to confirm the imaging function that can be used in wireless communication, and there is a problem in that an imaging efficiency is poor.

An object of the technology of the present disclosure is to provide a radiography system, an operation method thereof, and an operation program that make it possible to improve an imaging efficiency in a case of switching from wired communication to wireless communication.

In order to achieve the above object, according to the present disclosure, there is provided a radiography system that has still image capturing, fluoroscopy, and continuous still image capturing as imaging modes, the radiography system comprising: a radiography apparatus that has wired communication and wireless communication as communication modes; a radiation irradiation device that irradiates the radiography apparatus with radiation; and a processor provided inside or outside the radiography apparatus, in which the processor is configured to execute at least one of the following: prohibiting the fluoroscopy and permitting the still image capturing and the continuous still image capturing in accordance with switching of the communication mode from the wired communication to the wireless communication; limiting a frame rate during the continuous still image capturing to a predetermined value or less; and disabling an auto exposure control function, which transmits an irradiation stop signal for stopping irradiation with the radiation via the radiation irradiation device at a point in time at which a cumulative irradiation dose with which the radiography apparatus is irradiated reaches an appropriate amount.

It is preferable that the radiography apparatus is a portable type and is attachable to and detachable from an imaging table.

It is preferable that the processor is configured to switch the communication mode based on whether or not the radiography apparatus is mounted on the imaging table.

It is preferable that the processor is configured to switch the communication mode from the wired communication to the wireless communication in accordance with detachment of the radiography apparatus from the imaging table.

It is preferable that the radiography system further comprises a control device including an operation panel that is operated by a user and configured to control the radiation irradiation device and the radiography apparatus, and the radiography apparatus performs the wired communication or the wireless communication with the control device.

It is preferable that the processor is configured to enable a scattered radiation reduction function of reducing scattered radiation by performing image processing on a radiation image generated by the radiography apparatus in accordance with switching of the communication mode from the wired communication to the wireless communication.

According to the present disclosure, there is provided an operation method of a radiography system that has still image capturing, fluoroscopy, and continuous still image capturing as imaging modes and includes a radiography apparatus that has wired communication and wireless communication as communication modes, a radiation irradiation device that irradiates the radiography apparatus with radiation, and a processor provided inside or outside the radiography apparatus, the operation method comprising: causing the processor to execute at least one of the following: prohibiting the fluoroscopy and permitting the still image capturing and the continuous still image capturing in accordance with switching of the communication mode from the wired communication to the wireless communication; limiting a frame rate during the continuous still image capturing to a predetermined value or less; and disabling an auto exposure control function, which transmits an irradiation stop signal for stopping irradiation with the radiation via the radiation irradiation device at a point in time at which a cumulative irradiation dose with which the radiography apparatus is irradiated reaches an appropriate amount.

According to the present disclosure, there is provided an operation program for operating a radiography system that has still image capturing, fluoroscopy, and continuous still image capturing as imaging modes and includes a radiography apparatus that has wired communication and wireless communication as communication modes, a radiation irradiation device that irradiates the radiography apparatus with radiation, and a processor provided inside or outside the radiography apparatus, the operation program causing the processor to execute a process comprising at least one of the following: prohibiting the fluoroscopy and permitting the still image capturing and the continuous still image capturing in accordance with switching of the communication mode from the wired communication to the wireless communication; limiting a frame rate during the continuous still image capturing to a predetermined value or less; and disabling an auto exposure control function, which transmits an irradiation stop signal for stopping irradiation with the radiation via the radiation irradiation device at a point in time at which a cumulative irradiation dose with which the radiography apparatus is irradiated reaches an appropriate amount.

According to the technology of the present disclosure, it is possible to provide a radiography system, an operation method thereof, and an operation program that make it possible to improve an imaging efficiency in a case of switching from the wired communication to the wireless communication.

BRIEF DESCRIPTION OF THE DRAWINGS

Exemplary embodiments according to the technique of the present disclosure will be described in detail based on the following figures, wherein:

FIG. 2 is a diagram showing an example of disposition of each device in an imaging room, FIG. 4 is a diagram showing an example of an internal configuration of an imaging system, FIG. 11 is a diagram showing an example in which an operation restricted in wireless communication is compared with a case of wired communication, and FIG. 12 is a diagram showing another example in which the operation restricted in the wireless communication is compared with a case of the wired communication.

DETAILED DESCRIPTION

An example of an embodiment according to the technology of the present disclosure will be described with reference to the accompanying drawings.

Figure 1:
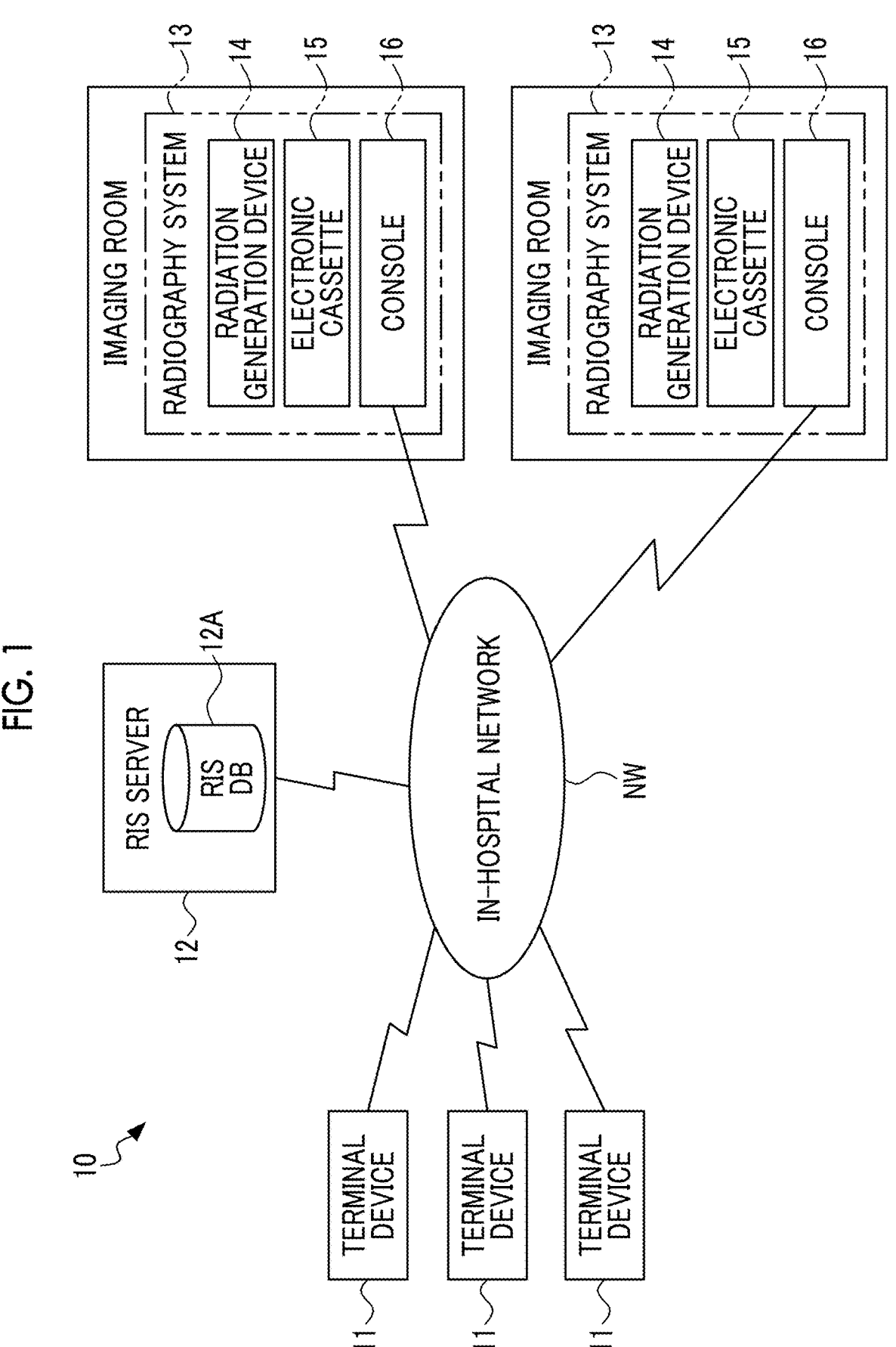
FIG. 1 is a diagram schematically showing a configuration of a radiology information system.

FIG. 1 schematically shows a configuration of a radiology information system (RIS) 10. The RIS 10 is a system for managing information, such as medical reservation and diagnostic record, in a radiology department, and constitutes a part of a hospital information system (hereinafter, referred to as a "HIS").

The RIS 10 includes a plurality of imaging request terminal devices (hereinafter, referred to as "terminal devices") 11, an RIS server 12, and radiography systems (hereinafter, referred to as "imaging systems") 13 individually installed in imaging rooms in a hospital, and is configured by connecting each of the terminal devices 11, the RIS server 12, and the imaging systems 13 to an in-hospital network NW configured by a wired or wireless local area network (LAN) or the like. The RIS 10 constitutes a part of the HIS provided in the same hospital, and an HIS server (not shown) that manages the entire HIS is also connected to the in-hospital network NW.

The terminal device 11 is a device for a user such as a doctor or a radiology technician to input or view diagnosis information or facility reservation, and an imaging request or imaging reservation of a radiation image is also made via the terminal device 11. Each terminal device 11 includes a personal computer having a display device and is capable of performing mutual communication with the RIS server 12 via the in-hospital network NW.

Meanwhile, the RIS server 12 receives the imaging request from each terminal device 11, manages an imaging schedule of the radiation image in the imaging system 13, and includes a database 12A.

The database 12A includes information on a subject, such as attribute information (name, gender, date of birth, age, blood type, weight, subject identification (ID), and the like), medical history, medical examination history, and a radiation image captured in the past.

The imaging system 13 captures the radiation image by an operation of the user in response to an instruction from the RIS server 12. The imaging system 13 comprises a radiation generation device 14, an electronic cassette 15, and a console 16. A radiation source 60 (see FIG. 2) generates radiation (for example, X-rays) to irradiate the subject with the radiation. The electronic cassette 15 absorbs the radiation transmitted through a site to be imaged of the subject to generate charges and generates a radiation image based on the generated charges. The console 16 controls the radiation generation device 14 and the electronic cassette 15. The electronic cassette 15 is an example of a "radiography apparatus" according to the technology of the present disclosure. The console 16 is an example of a "control device" according to the technology of the present disclosure.

Figure 2:
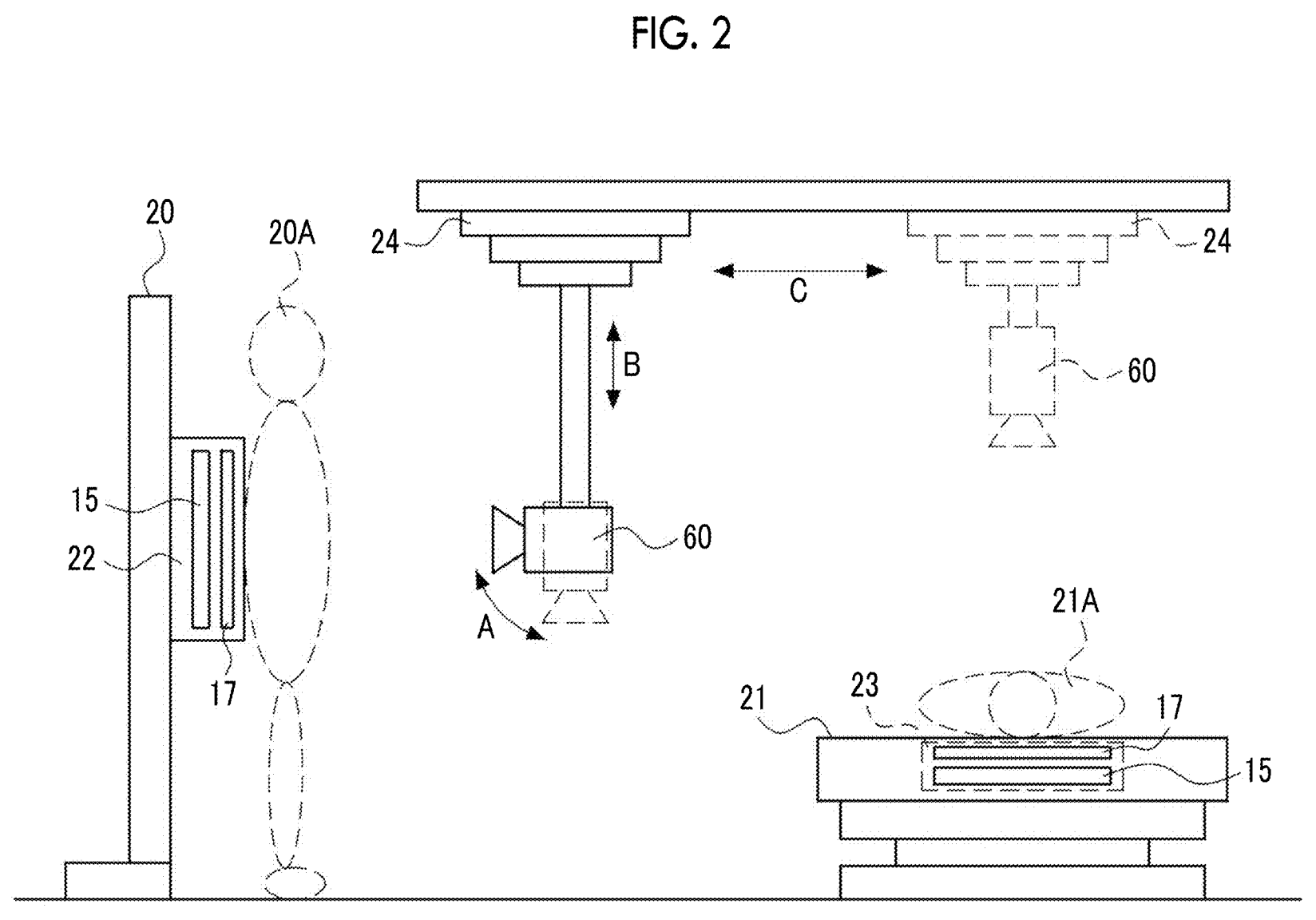

FIG. 2 shows an example of disposition of each device in the imaging room. As shown in FIG. 2, in the imaging room, the radiation source 60 of the radiation generation device 14, an upright imaging stand 20 used in a case where radiography in an upright posture is performed, and a decubitus imaging table 21 used in a case where radiography in a decubitus posture is performed are installed. A space on a front side of the upright imaging stand 20 is an imaging position 20A of the subject in a case where radiography is performed in an upright posture. A space on an upper side of the decubitus imaging table 21 is an imaging position 21A of the subject in a case where radiography is performed in a decubitus posture.

The electronic cassette 15 is a portable type and can be attached to and detached from the upright imaging stand 20 and the decubitus imaging table 21. The upright imaging stand 20 is provided with a holder 22 for mounting the electronic cassette 15. In a case where the radiation image is captured in the upright posture, the electronic cassette 15 is mounted on the holder 22. In a case where the radiation image is captured in the decubitus posture, the electronic cassette 15 is mounted on a holder 23 of the decubitus imaging table 21.

In addition, the holders 22 and 23 are configured such that a scattered radiation removal grid 17 can be mounted on a radiation incident side of the electronic cassette 15.

In addition, the imaging room is provided with a support moving mechanism 24 in order to enable radiography in an upright posture and a decubitus posture by one radiation source 60. The support moving mechanism 24 supports the radiation source 60 to be rotatable about a horizontal axis (direction of an arrow A), to be movable in a vertical direction (direction of an arrow B), and to be movable in a horizontal direction (direction of an arrow C).

The support moving mechanism 24 comprises a drive source that rotates the radiation source 60 about a horizontal axis, a drive source that moves the radiation source 60 in a vertical direction, and a drive source that moves the radiation source 60 in a horizontal direction (none of which are shown). The support moving mechanism 24 moves the radiation source 60 to a position facing the electronic cassette 15 in accordance with a posture of the subject during imaging.

The electronic cassette 15 is housed in a cradle (not shown) in a non-use state to charge a built-in battery. In a case of capturing the radiation image, the electronic cassette 15 is taken out from the cradle by the user and is mounted on the holder 22 of the upright imaging stand 20 in a case where an imaging posture is an upright posture, or is mounted on the holder 23 of the decubitus imaging table 21 in a case where the imaging posture is a decubitus posture.

Figure 3:
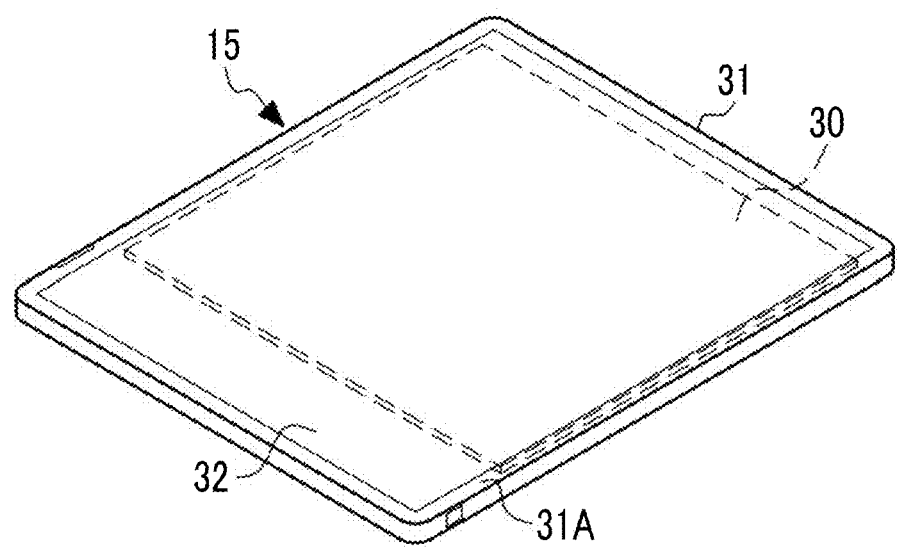
FIG. 3 is a diagram schematically showing a configuration of an electronic cassette.

FIG. 3 schematically shows a configuration of the electronic cassette 15. The electronic cassette 15 includes a radiation detector 30 and a housing 31. The radiation detector 30 detects the radiation transmitted through a site to be imaged of the subject and outputs a radiation image. The housing 31 has a flat box shape and accommodates the radiation detector 30 therein. The housing 31 is made of, for example, a conductive resin. In the housing 31, a rectangular opening is formed in a front surface 31A as an incident surface on which the radiation is incident, and a radiation transmission plate 32 is attached to the opening. The radiation transmission plate 32 is made of, for example, a carbon material that is lightweight, has high rigidity, and has high radiation transmittance.

The housing 31 also functions as an electromagnetic shield for preventing electromagnetic noise from entering the electronic cassette 15 and electromagnetic noise from being emitted from the electronic cassette 15 to the outside. In addition, a battery (for example, a secondary battery) that supplies power for driving the electronic cassette 15 and an antenna for performing wireless communication with the console 16 are provided in the housing 31. In addition, the electronic cassette 15 is provided with a connector (not shown) for wired connection to the console 16.

For example, the housing 31 has a size conforming to the international standard ISO 4090:2001 which is substantially the same as that of a film cassette or an IP cassette. The electronic cassette 15 is mounted on the holder 22 of the upright imaging stand 20 or the holder 23 of the decubitus imaging table 21 such that the front surface 31A of the housing 31 is held in a posture facing the radiation source 60. The electronic cassette 15 can also be used in a state of being detached from the upright imaging stand 20 or the decubitus imaging table 21.

Figure 4:
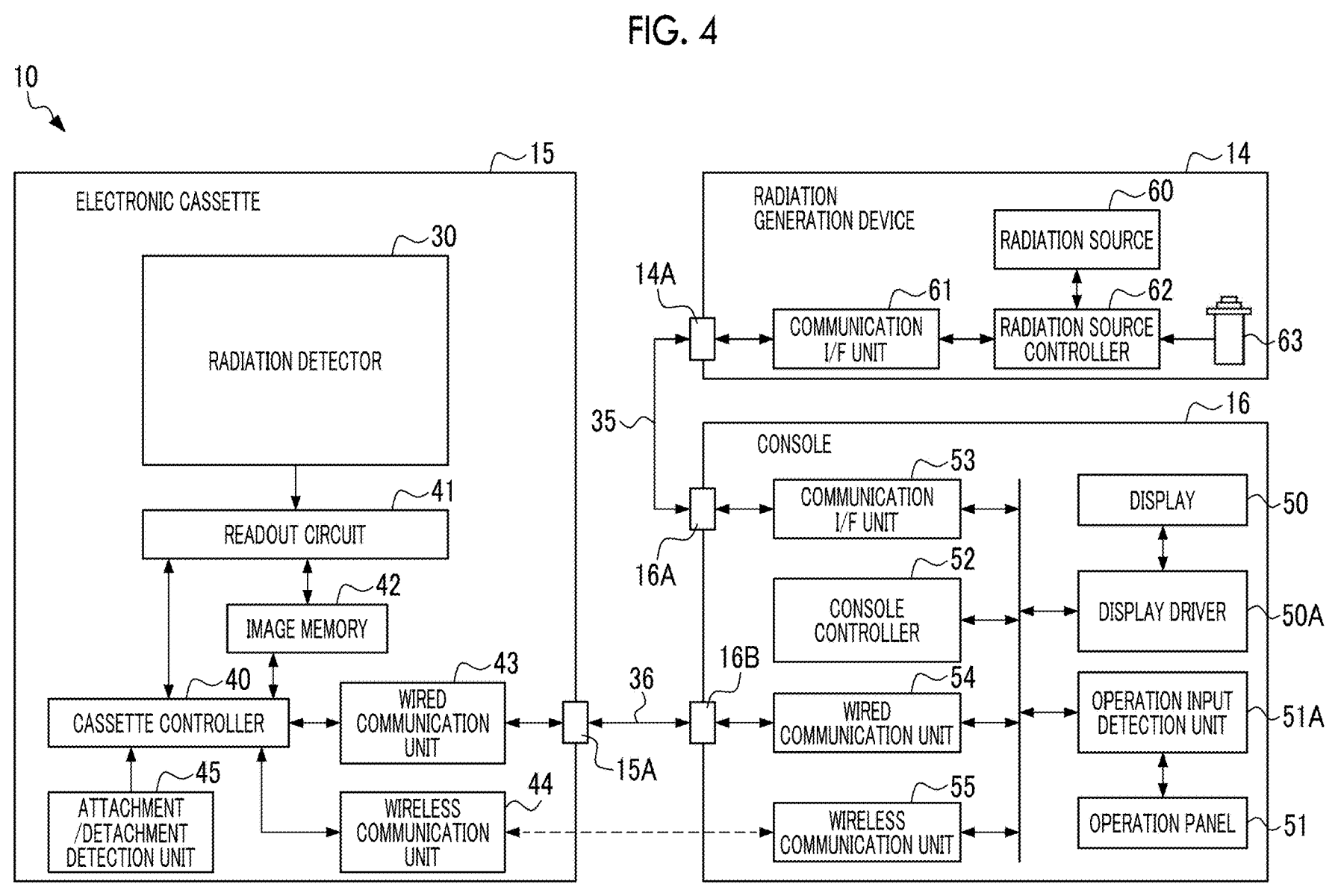

FIG. 4 shows an example of an internal configuration of the imaging system 13. The radiation generation device 14 is provided with a connection terminal 14A for performing communication with the console 16. The console 16 is provided with a connection terminal 16A for performing communication with the radiation generation device 14 and a connection terminal 16B for performing communication with the electronic cassette 15. The connection terminal 14A of the radiation generation device 14 and the connection terminal 16A of the console 16 are connected by a cable 35.

In a case of performing wired communication, a cable 36 is connected to the connection terminal 15A of the electronic cassette 15, and the electronic cassette 15 is connected to the console 16 via the cable 36.

The electronic cassette 15 includes the radiation detector 30, a cassette controller 40, a readout circuit 41, an image memory 42, a wired communication unit 43, a wireless communication unit 44, and an attachment/detachment detection unit 45. The radiation detector 30 detects the incident radiation to generate a radiation image.

The cassette controller 40 integrally controls each unit in the electronic cassette 15. The readout circuit 41, the image memory 42, the wired communication unit 43, the wireless communication unit 44, and the attachment/detachment detection unit 45 are connected to the cassette controller 40.

The readout circuit 41 drives the radiation detector 30 to read out the radiation image based on the control from the cassette controller 40. The image memory 42 stores the radiation image read out by the readout circuit 41.

The wired communication unit 43 is connected to the connection terminal 15A and transmits and receives various kinds of information to and from the console 16 via the cable 36. The wireless communication unit 44 is compatible with a wireless local area network (LAN) standard represented by the Institute of Electrical and Electronics Engineers (IEEE) 802.11a/b/g/n/ac, and transmits and receives various kinds of information to and from the console 16 by wireless communication.

The cassette controller 40 can communicate with the console 16 via the wired communication unit 43 or the wireless communication unit 44, and transmits and receives various kinds of information to and from the console 16. The cassette controller 40 controls the radiation detector 30 based on an exposure condition described below received from the console 16 via the wired communication unit 43 or the wireless communication unit 44. In addition, the cassette controller 40 transmits the radiation image stored in the image memory 42 to the console 16 via the wired communication unit 43 or the wireless communication unit 44.

The attachment/detachment detection unit 45 detects whether or not the electronic cassette 15 is mounted on the holder 22 of the upright imaging stand 20 or the holder 23 of the decubitus imaging table 21, and outputs a detection signal thereof to the cassette controller 40. For example, the attachment/detachment detection unit 45 is a switch that detects attachment and detachment based on a mechanical connection state or an electrical connection state between the holder 22 or the holder 23 and the connector provided in the electronic cassette 15. Hereinafter, in a case where the electronic cassette 15 is mounted on the holder 22 or the holder 23, it is said to be "mounted on the imaging table", and in a case where the electronic cassette 15 is detached from the holder 22 or the holder 23, it is said to be "detached from the imaging table". The attachment/detachment detection unit 45 may be provided in the holder 22 of the upright imaging stand 20 or the holder 23 of the decubitus imaging table 21.

In a case where the electronic cassette 15 is mounted on the imaging table, the cassette controller 40 enables wired communication by the wired communication unit 43 and disables wireless communication by the wireless communication unit 44. In a case where the electronic cassette 15 is detached from the imaging table, the cassette controller 40 disables wired communication by the wired communication unit 43 and enables wireless communication by the wireless communication unit 44. That is, in a case where the electronic cassette 15 is mounted on the imaging table, a communication mode becomes wired communication, and in a case where the electronic cassette 15 is detached from the imaging table, a communication mode becomes wireless communication.

In addition, as will be described in detail later, the cassette controller 40 performs control of selecting an imaging function suitable for wireless communication in accordance with switching of the communication mode from wired communication to wireless communication. In addition, in a case where an AEC function to be described later is enabled (that is, in an ON state), the cassette controller 40 transmits an irradiation stop signal to the console 16.

The console 16 is configured as a server computer, and comprises a display 50 that displays an operation menu, a captured radiation image, and the like, and an operation panel 51 that includes a plurality of keys and receives various kinds of information, operation instructions, and the like from a user.

In addition, the console 16 comprises a console controller 52, a display driver 50A, an operation input detection unit 51A, a communication interface (I/F) unit 53, a wired communication unit 54, and a wireless communication unit 55. The display driver 50A controls the display of various kinds of information on the display 50 based on the control from the console controller 52. The operation input detection unit 51A detects the information input to the operation panel 51 and outputs the information to the console controller 52.

The communication I/F unit 53 is connected to the connection terminal 16A and transmits and receives various kinds of information to and from the radiation generation device 14 via the cable 35. The wired communication unit 54 is connected to the connection terminal 16B and transmits and receives various kinds of information to and from the electronic cassette 15 via the cable 36. The wireless communication unit 55 is compatible with the wireless LAN standard described above, and transmits and receives various kinds of information to and from the electronic cassette 15 by wireless communication.

The console controller 52 can communicate with the radiation generation device 14 via the communication I/F unit 53, and transmits various kinds of information such as an exposure condition to the radiation generation device 14. In addition, the console controller 52 can communicate with the electronic cassette 15 via the wired communication unit 54 or the wireless communication unit 55, and transmits and receives various kinds of information to and from the console 16. The console controller 52 transmits a synchronization signal to the radiation generation device 14 and the electronic cassette 15, receives an irradiation stop signal, a radiation image, or the like from the electronic cassette 15, and transmits an exposure condition, the irradiation stop signal, or the like to the radiation generation device 14.

The radiation generation device 14 comprises the radiation source 60 that generates radiation, a communication I/F unit 61, a radiation source controller 62, and an irradiation switch 63. The communication I/F unit 61 is connected to the connection terminal 14A and transmits and receives various kinds of information to and from the console 16 via the cable 35. The radiation source controller 62 receives an exposure condition from the console 16 via the communication I/F unit 61 and causes the radiation source 60 to generate radiation based on the received exposure condition.

The radiation generation device 14 is an example of a "radiation irradiation device" according to the technology of the present disclosure.

The irradiation switch 63 is operated by the user. The radiation source controller 62 causes the radiation source 60 to generate the radiation in response to the operation of the irradiation switch 63 by the user. The irradiation switch 63 includes a switch used in a case of still image capturing or continuous still image capturing described below and a foot switch used in a case of fluoroscopy.

Figure 5:
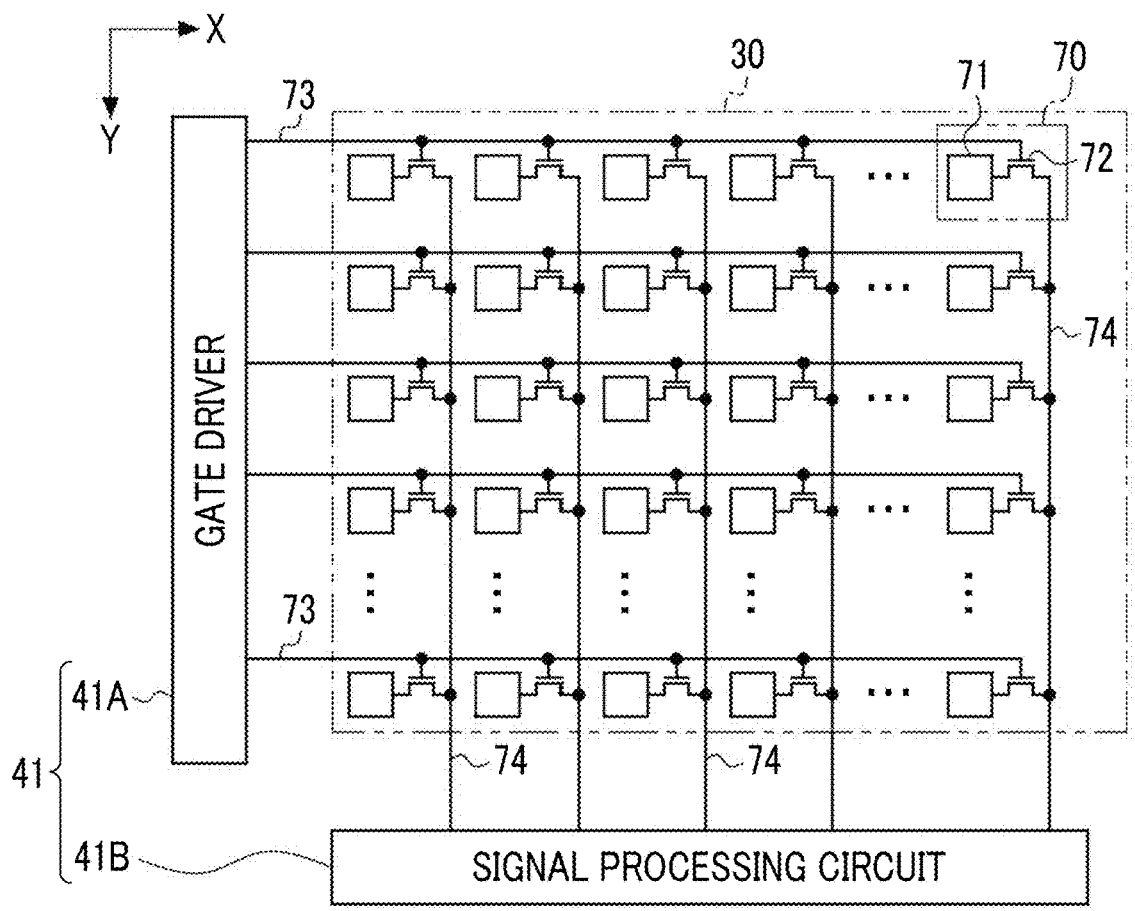
FIG. 5 is a diagram showing a configuration example of a radiation detector and a readout circuit.

FIG. 5 shows a configuration example of the radiation detector 30 and the readout circuit 41. The readout circuit 41 is composed of a gate driver 41A and a signal processing circuit 41B.

The radiation detector 30 includes a plurality of pixels 70 arranged on a matrix along an X direction and a Y direction orthogonal to each other. The pixel 70 is an element that generates and accumulates charges in accordance with an amount of incident radiation. A scintillator (not shown) that converts radiation into visible light is provided in a pixel region in which the plurality of pixels 70 are formed.

The pixel 70 includes a photoelectric conversion unit 71 that performs photoelectric conversion on the visible light converted by the scintillator to generate and accumulate the charges and a TFT 72 as a switching element. Each pixel 70 is connected to an intersection portion of a scanning line 73 and a signal line 74. A gate electrode of the TFT 72 is connected to the scanning line 73, and a source electrode of the TFT 72 is connected to the signal line 74. A drain electrode of the TFT 72 is connected to the photoelectric conversion unit 71. The scanning line 73 is connected to the gate driver 41A. The signal line 74 is connected to the signal processing circuit 41B.

The charges accumulated in the photoelectric conversion unit 71 of the pixel 70 by the incidence of the radiation are output to the signal processing circuit 41B via the signal line 74 in a case where the TFT 72 is turned on by the gate driver 41A via the scanning line 73.

The signal processing circuit 41B includes a charge amplifier, a correlated double sampling (CDS) circuit, an analog/digital (A/D) converter, and the like, and performs signal processing based on the charges output from the respective pixels 70. The image memory 42 described above stores signals for one frame output from the signal processing circuit 41B as the radiation image.

The radiation detector 30 is not limited to an indirect conversion type that converts radiation into light by the scintillator and converts the converted light into charges, and may be a direct conversion type using a conversion layer (for example, amorphous selenium) that directly converts radiation into charges.

Figure 6:
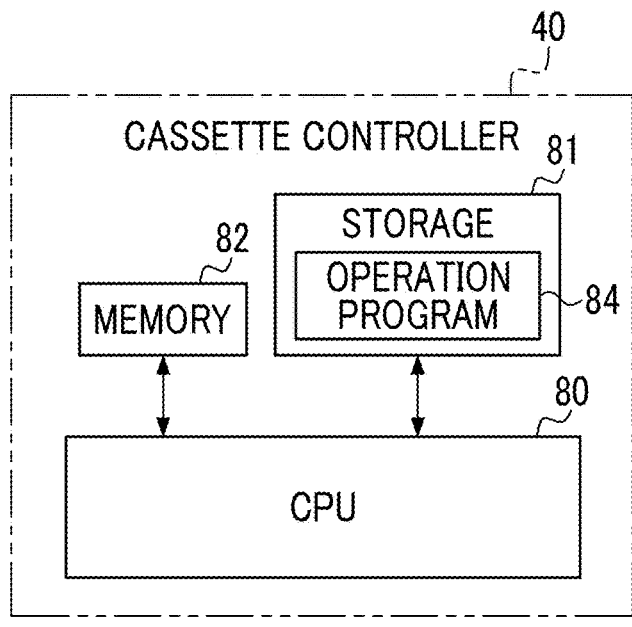
FIG. 6 is a diagram showing a configuration example of a cassette controller.

FIG. 6 shows a configuration example of the cassette controller 40. The cassette controller 40 is configured with, for example, a central processing unit (CPU) 80, a storage 81, and a memory 82. The storage 81 stores an operation program 84 and various kinds of data. The storage 81 is a non-volatile storage device such as a flash memory. The memory 82 is a volatile storage device such as a dynamic random access memory (DRAM) and is used as a work memory. The CPU 80 operates each unit based on the operation program 84 to implement various functions. The CPU 80 is an example of a "processor" according to the technology of the present disclosure.

The configuration of the console controller 52 is the same as the configuration of the cassette controller 40. The console controller 52 is configured with, for example, a CPU, a storage that stores an operation program, and a memory.

The imaging system 13 has still image capturing, fluoroscopy, and continuous still image capturing as imaging modes. The still image capturing is a mode in which one time of radiation imaging is performed in accordance with the operation of the irradiation switch 63. The fluoroscopy is a mode in which the radiography is continuously performed while the irradiation switch 63 is operated. The continuous still image capturing is a mode in which a plurality of times of still image capturing is continuously performed in accordance with the operation of the irradiation switch 63.

The user can designate any one of still image capturing, fluoroscopy, or continuous still image capturing as the imaging mode by operating the operation panel 51. In addition, in a case where the user designates the fluoroscopy, the user can designate continuous irradiation or pulse irradiation by operating the operation panel 51. The continuous irradiation is an irradiation method in which the radiation generation device 14 continuously applies the radiation during the fluoroscopy. The pulse irradiation is an irradiation method in which the radiation generation device 14 applies the radiation in a pulsed manner in synchronization with a frame rate of imaging during the fluoroscopy.

In a case where the user designates the still image capturing as the imaging mode, the user can designate an exposure condition, such as a tube voltage, a tube current, and an irradiation period in a case of applying the radiation, by operating the operation panel 51. In addition, in a case where the user designates the fluoroscopy as the imaging mode, the user can designate an exposure condition, such as a frame rate, a tube voltage, and a radiation dose to be applied, by operating the operation panel 51. Further, in a case where the user designates the continuous still image capturing as the imaging mode, the user can designate the number of times of imaging executed in one time of continuous still image capturing and a frame rate (specifically, the number of times of repeating the still image capturing per second) by operating the operation panel 51, in addition to the exposure condition of the still image capturing. The designated exposure condition is transmitted from the console 16 to the radiation generation device 14 and the electronic cassette 15.

Figure 7:
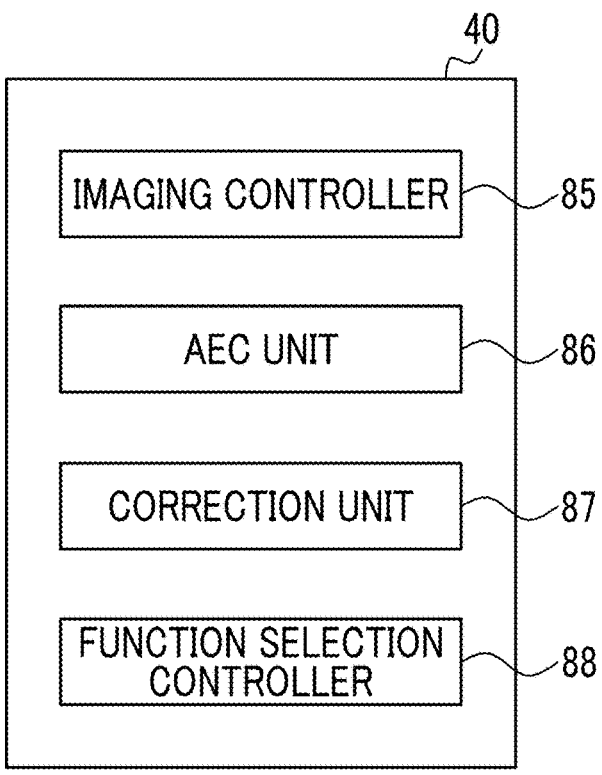
FIG. 7 is a diagram showing an example of a functional configuration of the cassette controller.

FIG. 7 shows an example of a functional configuration of the cassette controller 40. The cassette controller 40 functions as an imaging controller 85, an AEC unit 86, a correction unit 87, and a function selection controller 88. The imaging controller 85 operates the radiation detector 30 by controlling the readout circuit 41 based on the frame rate, the number of times of imaging, and the like included in the exposure condition transmitted from the console 16.

The AEC unit 86 performs control of monitoring a cumulative irradiation dose of the radiation from the radiation generation device 14 to the electronic cassette 15 and transmitting an irradiation stop signal for stopping radiation irradiation at a point in time at which the cumulative irradiation dose (that is, a reaching dose) reaches an appropriate amount. Specifically, in a case where the radiation incident on the radiation detector 30 is detected by the pixels 70, the AEC unit 86 starts to calculate the cumulative irradiation dose and transmits the irradiation stop signal to the console 16 at a point in time at which the cumulative irradiation dose reaches an appropriate amount calculated based on the exposure condition. In a case where the irradiation stop signal is received, the console 16 causes the radiation generation device 14 to stop the irradiation with the radiation.

The correction unit 87 executes offset correction of correcting the radiation image based on offset data acquired in advance. The offset data is correction data for correcting dark current noise and fixed pattern noise included in the radiation image. The offset data is stored in, for example, the storage 81. In addition, the correction unit 87 can execute offset calibration of acquiring the offset data by operating the radiation detector 30 in a state in which the radiation is not applied.

Figure 8:
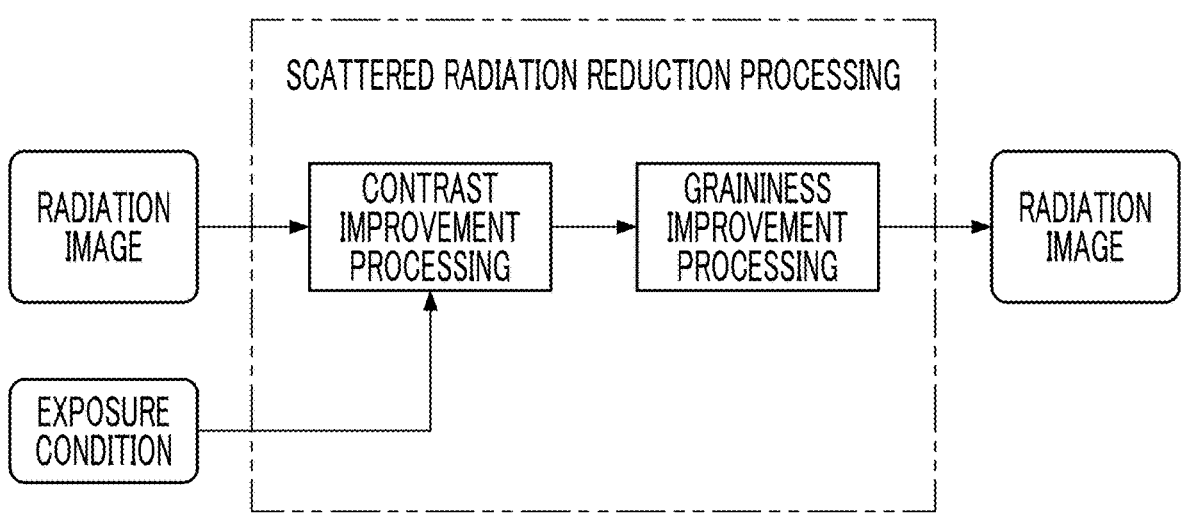
FIG. 8 is a diagram illustrating scattered radiation reduction processing.

In addition, the correction unit 87 can execute scattered radiation reduction processing shown in FIG. 8. The scattered radiation reduction processing is processing of reducing scattered radiation from the radiation image by performing image processing on the radiation as in a case of using the scattered radiation removal grid 17. For example, the scattered radiation reduction processing is divided into contrast improvement processing and graininess improvement processing. The contrast improvement processing is processing of improving a contrast of the radiation image by generating a scattered radiation estimated image based on the radiation image and the exposure condition (tube voltage, radiation dose, imaging distance, and the like) and subtracting the scattered radiation estimated image from the radiation image. The graininess improvement processing is processing of suppressing a graininess component from the radiation image in which the contrast has been improved. The scattered radiation reduction processing may be performed by the console 16 or an image processing device connected to the console 16.

The function selection controller 88 performs control of selecting an imaging function suitable for wireless communication in accordance with switching of the communication mode from the wired communication to the wireless communication in a case where the electronic cassette 15 is detached from the imaging table. Specifically, the function selection controller 88 prohibits fluoroscopy and permits still image capturing and continuous still image capturing as the imaging mode in response to switching of the communication mode from the wired communication to the wireless communication. That is, in a case where the communication mode is switched from the wired communication to the wireless communication, and the user sets the imaging mode by operating the operation panel 51, the fluoroscopy cannot be designated, and the still image capturing or the continuous still image capturing can be designated. Since the still image capturing and the continuous still image capturing are also permitted in the wired communication, the still image capturing and the continuous still image capturing are not only permitted in accordance with switching from the wired communication to the wireless communication.

In the fluoroscopy, it is necessary to perform the imaging while the radiation generation device 14 and the electronic cassette 15 are synchronized, and since a communication state is unstable in the wireless communication as compared with the wired communication, the fluoroscopy is prohibited in the wireless communication. In addition, in the fluoroscopy, the radiation generation device 14 and the electronic cassette 15 must be positioned to satisfy a standard such that a misregistration does not occur in an irradiation field of radiation. In a case where the electronic cassette 15 is detached from the imaging table to perform the fluoroscopy, it is difficult for the user to accurately perform positioning to satisfy the standard. Therefore, the fluoroscopy is prohibited.

In addition, the function selection controller 88 limits a frame rate during the continuous still image capturing to a predetermined value or less (for example, 2 fps or less) in accordance with switching from the wired communication to the wireless communication. Since a communication state is unstable in wireless communication as compared with wired communication, it is not possible to perform data communication having a large capacity, and there is a concern that communication is impossible in a case where the frame rate is higher than a predetermined value.

In addition, the function selection controller 88 disables the AEC function (that is, in an OFF state) in accordance with switching from the wired communication to the wireless communication. This is because the wireless communication has an unstable communication state as compared with the wired communication, and thus there is a possibility that the irradiation stop signal transmitted from the electronic cassette 15 to the console 16 is not received by the console 16. In a case where the console 16 does not receive the irradiation stop signal, the irradiation with the radiation is not stopped at an optimum timing, and the subject may be unnecessarily exposed to radiation.

Figure 9:
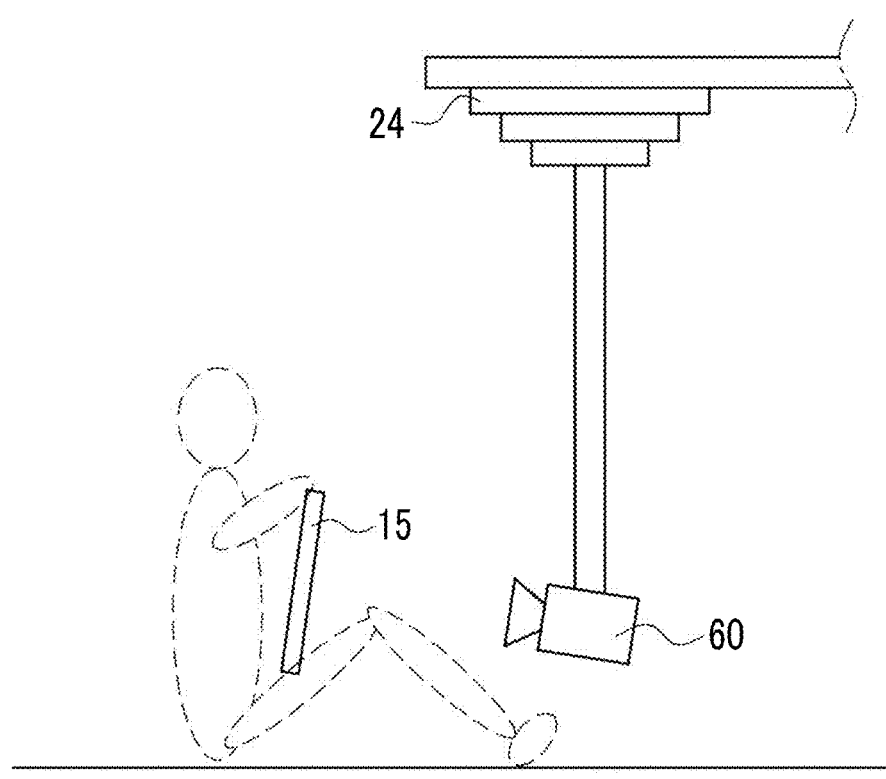
FIG. 9 is a diagram illustrating skyline imaging.

In addition, the function selection controller 88 enables the scattered radiation reduction function (that is, in an ON state) in response to switching from the wired communication to the wireless communication. This is because, in a case where the electronic cassette 15 is detached from the imaging table and used, the scattered radiation removal grid 17 is not used in many cases, and the scattered radiation reduction function is preferably used instead of the scattered radiation removal grid 17. For example, as shown in FIG. 9, in a case where the subject grips the electronic cassette 15 and is subjected to knee joint axial imaging (so-called skyline imaging), the scattered radiation removal grid 17 is not used in many cases in consideration of a burden on the subject. Therefore, in such a case, the burden on the subject is reduced by enabling the scattered radiation reduction function.

Information about the imaging function selected by the function selection controller 88 is transmitted to the console 16. The console controller 52 partially restricts the operation that can be performed by the operation panel 51 based on the information transmitted from the function selection controller 88. Specifically, in the wireless communication, only the still image capturing or the continuous still image capturing can be designated as the imaging mode, and only a value equal to or less than a predetermined value can be designated as the frame rate during the continuous still image capturing. In addition, in the wireless communication, since the AEC function is forcibly disabled, the operation is restricted such that the AEC function cannot be enabled. Further, in the wireless communication, the scattered radiation reduction function is forcibly enabled. Therefore, the operation is restricted such that the scattered radiation reduction function cannot be disabled.

The console controller 52 may display the information about the imaging function, which is limited in operation by switching from the wired communication to the wireless communication, on the display 50.

Figure 10:
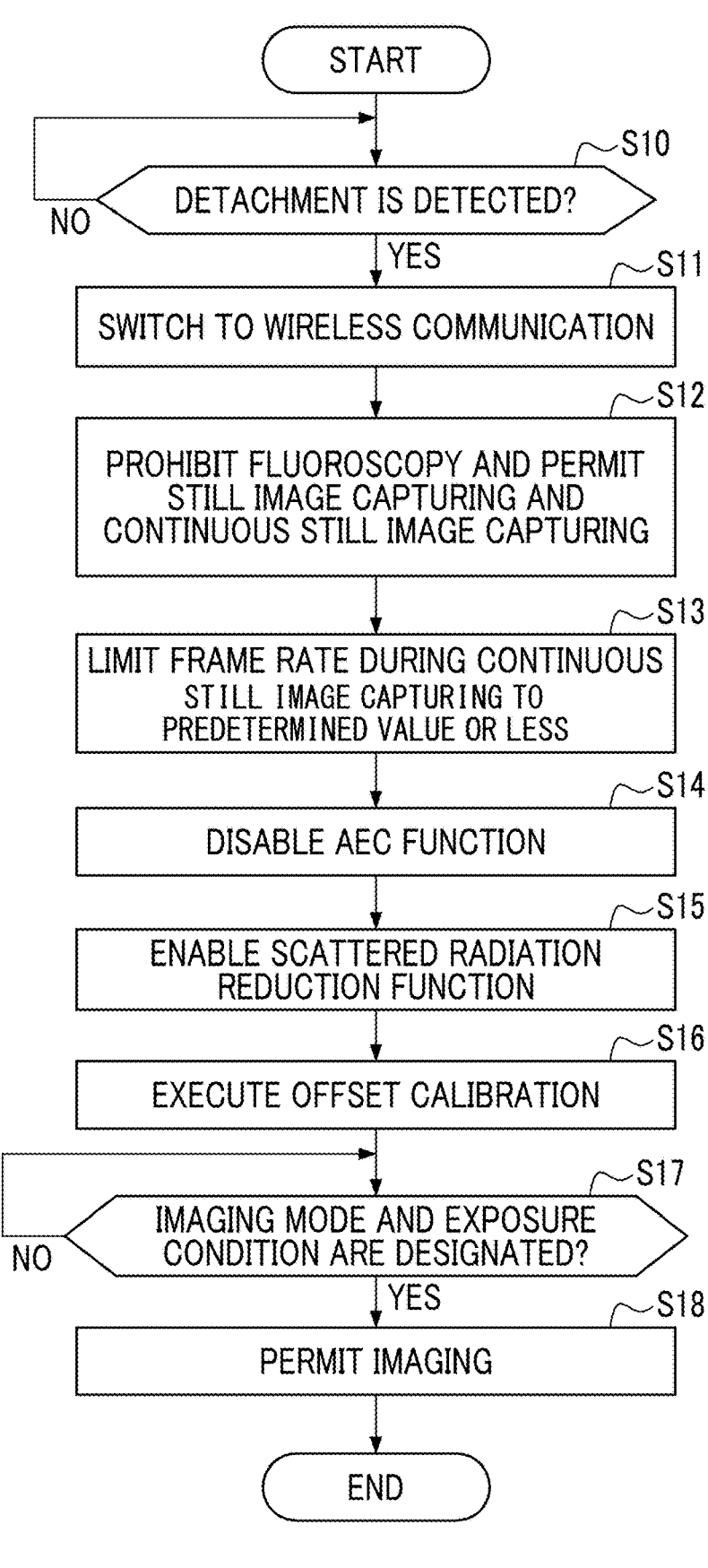
FIG. 10 is a diagram showing an example of a flow of a process in a case where the electronic cassette is detached from an imaging table.

FIG. 10 shows an example of a flow of a process in a case where the electronic cassette 15 is detached from the imaging table. First, the cassette controller 40 determines whether or not the electronic cassette 15 is detached from the imaging table based on the detection signal output by the attachment/detachment detection unit 45 in a state in which the electronic cassette 15 is mounted on the imaging table (step S10). In a case where the electronic cassette 15 is not detached from the imaging table (step S10: NO), the cassette controller 40 repeats the determination in step S10. In a case where the electronic cassette 15 is detached from the imaging table (step S10: YES), the cassette controller 40 switches the communication mode from the wired communication to the wireless communication (step S11).

Next, the cassette controller 40 prohibits the fluoroscopy and permits the still image capturing and the continuous still image capturing as the imaging mode (step S12). Next, the cassette controller 40 limits the frame rate during the continuous still image capturing to a predetermined value or less (step S13). Next, the cassette controller 40 disables the AEC function (step S14). Next, the cassette controller 40 enables the scattered radiation reduction function (step S15). The information about the imaging function selected by using switching of the communication mode from the wired communication to the wireless communication as a trigger is transmitted to the console 16. The order of steps S12 to S15 is not particularly limited, and some or all of steps S12 to S15 may be performed at the same time.

Thereafter, the cassette controller 40 executes the offset calibration (step S16). The offset calibration may be performed in response to the operation of the operation panel 51 by the user.

Next, the cassette controller 40 determines whether or not the imaging mode and the exposure condition are designated on the console 16 (step S17). In a case where the imaging mode and the exposure condition are not designated (step S17: NO), the cassette controller 40 repeats the determination in step S17. In a case where the imaging mode and the exposure condition are designated (step S17: YES), the cassette controller 40 permits imaging by transmitting a permission signal to the console 16 (step S18). Thereafter, it is possible to start imaging.

Thereafter, in a case where the electronic cassette 15 is mounted on the imaging table, the cassette controller 40 detects that the electronic cassette 15 is mounted on the imaging table based on the detection signal from the attachment/detachment detection unit 45, and switches the communication mode from the wireless communication to the wired communication. In the wired communication, the function selection controller 88 releases all the operation restrictions of the operation panel 51 that are restricted in the wireless communication.

FIG. 11 shows operations restricted in the wireless communication in comparison with a case of the wired communication. In the present embodiment, as described above, the cassette controller 40 prohibits the fluoroscopy and permits the still image capturing and the continuous still image capturing by using switching of the communication mode from the wired communication to the wireless communication as a trigger. However, the cassette controller 40 limits the frame rate during the continuous still image capturing to a predetermined value or less. In addition, the cassette controller 40 disables the AEC function and enables the scattered radiation reduction function by using switching of the communication mode from the wired communication to the wireless communication as a trigger. On the other hand, in the wired communication, the cassette controller 40 permits all of the still image capturing, the fluoroscopy, and the continuous still image capturing, and allows the selection of enabling/disabling of the AEC function and the scattered radiation reduction function.

As described above, according to the technology of the present disclosure, in a case of switching from the wired communication to the wireless communication, since the user does not need to perform work such as referring to an operation manual or the like to confirm an imaging function that can be used in the wireless communication, an imaging efficiency is improved.

In the embodiment described above, the cassette controller 40 enables the scattered radiation reduction function by using switching of the communication mode from the wired communication to the wireless communication as a trigger. However, as shown in FIG. 12, it may also be possible to select enabling/disabling of the scattered radiation reduction function even in the wireless communication. This is because the scattered radiation removal grid 17 may also be used in the wireless communication, and even in a case where the scattered radiation removal grid 17 is not used, there may be a case where the scattered radiation is little in a site of the subject where a body thickness is thin and it is not necessary to remove the scattered radiation, and the like.

That is, the cassette controller 40 may execute at least one of the following: prohibiting the fluoroscopy and permitting the still image capturing and the continuous still image capturing by using switching of the communication mode from the wired communication to the wireless communication as a trigger; limiting the frame rate during the still image capturing to a predetermined value or less; or disabling the AEC function.

In addition, the cassette controller 40 may change the frame rate in accordance with a radio wave situation of the wireless communication, in addition to limiting the frame rate during the continuous still image capturing to a predetermined value or less. For example, the cassette controller 40 may limit the frame rate during the continuous still image capturing to a predetermined value or less, and then further limit the frame rate in a case where the radio wave situation of the wireless communication is bad.

In addition, in the embodiment described above, the control of selecting the imaging function is mainly performed by the cassette controller 40, but may be mainly performed by the console controller 52. For example, the cassette controller 40 may transmit the detection signal output from the attachment/detachment detection unit 45 to the console 16, and the console controller 52 may perform the control of selecting the imaging function including changing the communication mode based on the detection signal. In addition, the cassette controller 40 may change the communication mode based on the detection signal output from the attachment/detachment detection unit 45, and the console controller 52 may perform the control of selecting the imaging function by detecting that the communication mode is changed by the cassette controller 40. The cassette controller 40 is an example of a "processor provided inside a radiography apparatus" according to the technology of the present disclosure. The console controller 52 is an example of a "processor provided outside the radiography apparatus".

In addition, the technology of the present disclosure can also be applied to a round-purpose radiography system including a mobile radiography apparatus. The mobile radiography system is a radiography system in which the radiation generation device 14 and the console 16 according to the embodiment described above are integrated and configured to be movable as a round cart. In the mobile radiography system, the electronic cassette is mainly used in the wireless communication as the communication mode. In emergency care or the like, there may be a case where radiography is desired to be performed without carrying an emergency patient to an imaging room. However, in the mobile radiography system, it is difficult to perform fluoroscopy because it is difficult to accurately position the radiation generation device and the electronic cassette.

However, since it may be desired to perform the continuous still image capturing for the emergency patient without requiring the fluoroscopy, it can be said that it is preferable to apply the technology of the present disclosure to the mobile radiography system.

In addition, the technology of the present disclosure is not limited to X-rays and can be applied to a system that images a subject using other types of radiation such as y-rays.

In the embodiment described above, for example, hardware structures of processing units that execute various kinds of processing, such as the cassette controller 40 and the console controller 52, are various processors as described below.

The various processors include a CPU, a programmable logic device (PLD), a dedicated electric circuit, and the like. The CPU is a general-purpose processor that executes software (program) and functions as various processing units, as is well known. The PLD is a processor capable of changing a circuit configuration after manufacture, such as a field programmable gate array (FPGA).

The dedicated electric circuit is a processor having a circuit configuration specially designed for executing specific processing, such as an application specific integrated circuit (ASIC).

One processing unit may be composed of one of the various processors or may be composed of a combination of two or more processors of the same type or different types (for example, a plurality of FPGAs or a combination of a CPU and an FPGA). A plurality of processing units may be composed of one processor. As an example of composing the plurality of processing units with one processor, first, there is a form in which one processor is composed of a combination of one or more CPUs and software, and the processor functions as the plurality of processing units. Second, there is a form in which a processor, which implements the functions of the entire system including the plurality of processing units with one IC chip, is used, as represented by a system on chip (SoC) or the like. As described above, the various processing units are configured using one or more of the above various processors as a hardware structure.

Furthermore, the hardware structure of the various processors is more specifically an electric circuit (circuitry) in which circuit elements such as semiconductor elements are combined.

The technology of the present disclosure is not limited to the embodiment described above and may adopt various configurations without departing from the spirit and scope of the present disclosure. Further, the technology of the present disclosure extends to a computer-readable storage medium that non-transitorily stores the program, in addition to the program.

The following technologies can be ascertained by the above description.

Additional Note 1

A radiography system that has still image capturing, fluoroscopy, and continuous still image capturing as imaging modes, the radiography system comprising: a radiography apparatus that has wired communication and wireless communication as communication modes; a radiation irradiation device that irradiates the radiography apparatus with radiation; and a processor provided inside or outside the radiography apparatus, in which the processor is configured to execute at least one of the following: prohibiting the fluoroscopy and permitting the still image capturing and the continuous still image capturing in accordance with switching of the communication mode from the wired communication to the wireless communication; limiting a frame rate during the continuous still image capturing to a predetermined value or less; and disabling an auto exposure control function, which transmits an irradiation stop signal for stopping irradiation with the radiation via the radiation irradiation device at a point in time at which a cumulative irradiation dose with which the radiography apparatus is irradiated reaches an appropriate amount.
Additional Note 2

The radiography system according to Additional note 1, in which the radiography apparatus is a portable type and is attachable to and detachable from an imaging table.
Additional Note 3

The radiography system according to Additional note 2, in which the processor is configured to switch the communication mode based on whether or not the radiography apparatus is mounted on the imaging table.
Additional Note 4

The radiography system according to Additional note 3, in which the processor is configured to switch the communication mode from the wired communication to the wireless communication in accordance with detachment of the radiography apparatus from the imaging table.
Additional Note 5

The radiography system according to any one of Additional notes 1 to 4, further comprising: a control device including an operation panel that is operated by a user and configured to control the radiation irradiation device and the radiography apparatus, in which the radiography apparatus performs the wired communication or the wireless communication with the control device.
Additional Note 6

The radiography system according to any one of Additional notes 1 to 5, in which the processor is configured to enable a scattered radiation reduction function of reducing scattered radiation by performing image processing on a radiation image generated by the radiography apparatus in accordance with switching of the communication mode from the wired communication to the wireless communication.

What is claimed is:

1. A radiography system that has still image capturing, fluoroscopy, and continuous still image capturing as imaging modes, the radiography system comprising:

a radiography apparatus that has wired communication and wireless communication as communication modes;
a radiation irradiation device that irradiates the radiography apparatus with radiation;
a processor provided inside or outside the radiography apparatus; and
a control apparatus including an operation panel that is operated by a user and configured to perform wired communication or wireless communication with the radiography apparatus,
wherein the processor is configured to, in response to switching the communication mode from a wired communication mode to a wireless communication mode, execute the following operations:
prohibiting the fluoroscopy and permitting the still image capturing and the continuous still image capturing;
limiting a frame rate during the continuous still image capturing to a predetermined value or less;
disabling an auto exposure control function, which transmits, via the wireless communication, an irradiation stop signal for stopping irradiation with the radiation via the radiation irradiation device at a point in time at which a cumulative irradiation dose with which the radiography apparatus is irradiated reaches an appropriate amount; and

performing an operation restriction using the operation panel such that selection of the fluoroscopy as an imaging mode, activation of the auto exposure control function, and setting of the frame rate exceeding the predetermined value are disabled.

2. The radiography system according to claim 1, wherein the radiography apparatus is a portable type and is attachable to and detachable from an imaging table.

3. The radiography system according to claim 2, wherein the processor is configured to switch the communication mode based on whether or not the radiography apparatus is mounted on the imaging table.

4. The radiography system according to claim 3, wherein the processor is configured to switch the communication mode from the wired communication to the wireless communication in accordance with detachment of the radiography apparatus from the imaging table.

5. The radiography system according to claim 1, wherein the processor is configured to enable a scattered radiation reduction function of reducing scattered radiation by performing image processing on a radiation image generated by the radiography apparatus in accordance with switching of the communication mode from the wired communication to the wireless communication.

6. An operation method of a radiography system that has still image capturing, fluoroscopy, and continuous still image capturing as imaging modes and includes a radiography apparatus that has wired communication and wireless communication as communication modes,
a radiation irradiation device that irradiates the radiography apparatus with radiation,
a processor provided inside or outside the radiography apparatus; and
a control apparatus including an operation panel that is operated by a user and configured to perform wired communication or wireless communication with the radiography apparatus, the operation method comprising:
causing the processor to, in response to switching the communication mode from a wired communication mode to a wireless communication mode, execute the following operations:
prohibiting the fluoroscopy and permitting the still image capturing and the continuous still image capturing;
limiting a frame rate during the continuous still image capturing to a predetermined value or less;
disabling an auto exposure control function, which transmits, via the wireless communication, an irradiation stop signal for stopping irradiation with the radiation via the radiation irradiation device at a point in time at which a cumulative irradiation dose with which the radiography apparatus is irradiated reaches an appropriate amount; and
performing an operation restriction using the operation panel such that selection of the fluoroscopy as an imaging mode, activation of the auto exposure control function, and setting of the frame rate exceeding the predetermined value are disabled.

7. A non-transitory computer-readable storage medium storing an operation program for operating a radiography system that has still image capturing, fluoroscopy, and continuous still image capturing as imaging modes and includes a radiography apparatus that has wired communication and wireless communication as communication modes, a radiation irradiation device that irradiates the radiography apparatus with radiation, a processor provided inside or outside the radiography apparatus, and a control apparatus including an operation panel that is operated by a user and configured to perform wired communication or wireless communication with the radiography apparatus, the operation program causing the processor to, in response to switching the communication mode from a wired communication mode to a wireless communication mode, execute a process comprising the following operations:

prohibiting the fluoroscopy and permitting the still image capturing and the continuous still image capturing;

limiting a frame rate during the continuous still image capturing to a predetermined value or less; and disabling an auto exposure control function, which transmits, via the wireless communication, an irradiation stop signal for stopping irradiation with the radiation via the radiation irradiation device at a point in time at which a cumulative irradiation dose with which the radiography apparatus is irradiated reaches an appropriate amount; and performing an operation restriction using the operation panel such that selection of the fluoroscopy as an imaging mode, activation of the auto exposure control function, and setting of the frame rate exceeding the predetermined value are disabled.

\* \* \* \* \*